US009091645B2

(12) United States Patent
Gumbrecht et al.

(10) Patent No.: US 9,091,645 B2
(45) Date of Patent: Jul. 28, 2015

(54) APPARATUS AND METHOD FOR THE DETECTION OF LIQUIDS OR SUBSTANCES FROM LIQUIDS, AND USE OF SAID APPARATUS

(75) Inventors: Walter Gumbrecht, Herzogenaurach (DE); Peter Paulicka, Röttenbach (DE); Manfred Stanzel, Erlangen (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 418 days.

(21) Appl. No.: 12/867,652

(22) PCT Filed: Feb. 9, 2009

(86) PCT No.: PCT/EP2009/051440
§ 371 (c)(1),
(2), (4) Date: Aug. 13, 2010

(87) PCT Pub. No.: WO2009/101048
PCT Pub. Date: Aug. 20, 2009

(65) Prior Publication Data
US 2010/0330699 A1  Dec. 30, 2010

(30) Foreign Application Priority Data
Feb. 15, 2008  (DE) .......................... 10 2008 009 185

(51) Int. Cl.
G01N 33/566  (2006.01)
G01N 15/04   (2006.01)
(Continued)

(52) U.S. Cl.
CPC ............ *G01N 27/40* (2013.01); *G01N 15/04* (2013.01); *G01N 27/30* (2013.01); *G01N 33/50* (2013.01); *G01N 33/566* (2013.01); *Y10T 436/143333* (2015.01)

(58) Field of Classification Search
CPC ..... G01N 33/50; G01N 33/566; G01N 15/04; G01N 27/00; G01N 27/30; G01N 27/40; B01D 67/0086; Y10T 436/143333
USPC ........... 436/63, 149, 150, 151, 152, 178, 177; 422/68.1; 204/409, 193, 400, 401, 402, 204/403.01, 403.02, 403.03, 403.04, 204/403.05, 403.06, 403.07, 403.08, 204/403.09, 403.1, 403.11, 403.12, 403.13, 204/403.14, 406, 407
See application file for complete search history.

(56) References Cited

U.S. PATENT DOCUMENTS 5,670,031 A    9/1997  Hintsche et al.
5,980,709 A *  11/1999  Hodges et al. ........... 204/403.06
(Continued)

FOREIGN PATENT DOCUMENTS

DE    42 36 421 A1    5/1994
DE    10058394        7/2002
(Continued)

OTHER PUBLICATIONS

Meyer, Heinrich et al. "Two-dimensional imaging of O2, H2O2, and glucose distributions by an array of 400 individually addressable microelectrodes." Analytical Chemistry (1995) 67 1164-1170.*
(Continued)

*Primary Examiner* — Christopher A Hixson
(74) *Attorney, Agent, or Firm* — Roberts Mlotkowski Safran & Cole, P.C.; David S. Safran

(57) ABSTRACT

The embodiments relate to an apparatus and a method for detecting liquids or substances from liquids in spatially separate reaction zones. The embodiments further relate to the use of the apparatus in a plug-in module or a chip card which can be used for rapid immunological tests, for example, with the help of a reading device. The liquids or substances from liquids are detected by means of a sensor array which includes at least two sensors and on which at least one diaphragm is arranged. Individual sensors are spatially separated from each other on a plane by means of walls. The diaphragm can be filled with liquid that is to be analyzed. Sealed reaction chambers are created when pressure is applied to the diaphragm. Pores in the diaphragm are completely closed in the zone of the walls while the pores are merely reduced in size and liquid can continue to be exchanged in zones directly above the sensors. No liquid can be exchanged between adjacent reaction chambers as long as the pressure is applied to and compresses the diaphragm. In the sealed reaction chambers, reactions can take place independently of reactions in adjacent reaction chamber. Reaction products or substances in the liquid can be measured with smaller measurement errors in sealed reaction chamber than when the liquid flows across the entire diaphragm.

12 Claims, 3 Drawing Sheets

(51) Int. Cl.
*G01N 27/00* (2006.01)
*G01N 33/50* (2006.01)
*G01N 27/40* (2006.01)
*G01N 27/30* (2006.01)

(56) References Cited

U.S. PATENT DOCUMENTS

| | | |
|---|---|---|
| 6,210,907 B1 | 4/2001 | Cha |
| 6,569,674 B1 | 5/2003 | McGarry et al. |
| 6,726,818 B2 | 4/2004 | Cui et al. |
| 2004/0029203 A1* | 2/2004 | Gumbrecht et al. ......... 435/7.92 |
| 2006/0105355 A1 | 5/2006 | Maurer |
| 2006/0108218 A1* | 5/2006 | Gephart et al. ............... 204/400 |

FOREIGN PATENT DOCUMENTS

| | | |
|---|---|---|
| DE | 101 17 723 A1 | 10/2002 |
| DE | 10126341 | 12/2002 |
| DE | 102006046776 | 4/2008 |
| WO | 9408236 | 4/1994 |
| WO | 9632635 | 10/1996 |
| WO | 0119505 | 3/2001 |
| WO | 02073153 | 9/2002 |

OTHER PUBLICATIONS

International Search Report issued Jun. 10, 2009 in corresponding International Application PCT/EP2009/051440.
Germany Office Action issued Mar. 10, 2008 in corresponding German Application No. 102008009185.5-52.

* cited by examiner

APPARATUS AND METHOD FOR THE DETECTION OF LIQUIDS OR SUBSTANCES FROM LIQUIDS, AND USE OF SAID APPARATUS

CROSS REFERENCE TO RELATED APPLICATIONS

This application is the U.S. national stage of International Application No. PCT/EP2009/051440, filed Feb. 9, 2009 and claims the benefit thereof. The International Application claims the benefits of German Application No. 102008009185.5 filed on Feb. 15, 2008, both applications are incorporated by reference herein in their entirety.

BACKGROUND

The embodiments relate to an apparatus and a method for the detection of liquids or substances from liquids in spatially different reaction regions. A corresponding apparatus and a method for the operation thereof are disclosed in DE 10058394 C1. The embodiments furthermore relate to the use thereof in a smart card which can be used with the aid of a read-out device for e.g. immunological fast tests. In this case, the liquids or substances from liquids are detected by means of a sensor array which is composed of at least two sensors and on which at least one membrane is arranged.

In biochemical analysis technology, sensor arrays having e.g. electrochemical or optical sensors are increasingly being used in order to test the composition of liquids such as e.g. blood or urine for specific substances rapidly and cost-effectively. Thus, DNA analyses can be performed by means of sensor arrays having sensors which are coated with different DNA catcher molecules. Urine samples from subjects can be examined for pathogens by virtue of the fact that, in sensor arrays, sensors are coated with antibodies and the specific binding of the pathogens to the corresponding antibodies is measured. In this case, one preferred measuring method is the electrochemical measurement of substance conversion that only occurs on specifically bound molecules.

In order to attain good handling of the sensor arrays, recent developments are aimed at integrating the sensor arrays into small, compact, portable systems such as smart cards, for example. The latter contain a chip with a sensor array integrated thereon, microfluidic channels for liquid transport to and away from the chip, reaction chambers for reactions such as e.g. disintegration of blood and subsequent polymerase chain reaction (PCR), and also chambers containing chemical reagents preferably in dry form. Standardized smart cards are constructed from plastic and can be introduced into analysis devices in a simple manner. Beforehand, the liquid to be examined that is taken from the patient is applied onto or introduced into the smart card, the dry reagents are dissolved and reactions necessary for the detection are initiated. When the smart card is introduced into the analysis device, the sensors on the chip are activated by the analysis device via electrical contacts on the smart card and can, under closed-loop or open-loop control, measure biochemical reactions and also output the results of the measurement to the analysis device in the form of optical or electrical signals. The result can then be output by the analysis device, after evaluation by a computer-aided unit, via a monitor or other indicator instruments.

In order to attain an increased measurement accuracy and a lower error rate during the measurement, the prior art, such as e.g. DE 10058394C1, discloses a method and an associated arrangement wherein the sensors of the sensor array are separated from one another during the measurement in such a way that no liquid can flow from one sensor to the other. The sensors of the sensor array are arranged on a planar surface with walls between the individual sensors, wherein the walls project from the surface. A housing upper part is arranged parallel to the planar surface of the sensor array at a distance from the walls, the housing upper part being at a sufficient distance from the surface and the walls to allow liquid to flow between the surface and the housing upper part. Before the measurement, the housing upper part is pressed in the direction of the surface with walls with the aid of a plunger, such that the walls and the housing upper part are in close contact.

The flowing of the liquid has been prevented, and closed-off reaction spaces, delimited by the planar surface, the walls and the housing upper part, have been produced above the sensors. The liquid which has been enclosed in the reaction spaces can then be examined without exchange of liquid between different reaction spaces. The measurement of the sensors takes place with the aid of the closed-off reaction spaces independently of one another.

The method described in the prior art in accordance with DE 10058394C1, for example, leads to a complicated arrangement with housing upper part and plunger wherein the walls between the sensors have to correspond to precise dimensions. These precise dimensions are difficult to realize in practice:

If the walls project too little from the planar surface in which the sensors are arranged, then this gives rise to reaction spaces which are too small and have an amount of liquid that is too small to carry out a meaningful measurement. The housing upper part can, under certain circumstances, be seated on the sensors at high plunger pressure, whereby the measurement is corrupted.

If the dimensions of the walls are made too large, then the sensors have to be arranged at a larger distance from one another, and the required amount of liquid for filling the arrangement increases. This means that the sensitivity of the measurement turns out to be lower and the number of sensors available for measurement decreases for the same area since the dimensions of the sensors have to be made larger in order to achieve a sufficient measurement accuracy.

SUMMARY

It is an aspect of the embodiment to specify a—compared with the prior art—simpler, and more cost-effective apparatus and method and the application thereof for the detection of liquids or substances in liquids. In particular, it is an aspect of the embodiments to reduce the dependence of the measurement accuracy on the fault tolerances of the production of the walls between the sensors. A simpler construction with fewer fault possibilities is intended to save costs in the production of the apparatus and to increase the measurement accuracy.

The apparatus according to the embodiment for the detection of liquids or substances from liquids in spatially different reaction regions or reaction spaces includes a sensor array composed of at least two sensors, and at least one membrane arranged on the sensor array and having permeable or semipermeable, porous properties. The advantages associated with this configuration of the apparatus can be seen, in particular, in its simple and cost-effective, reproducible construction in conjunction with, nevertheless, sufficient measurement accuracy.

In particular, the apparatus according to the embodiments includes at least one membrane whose permeability is adjustable depending on a tensile and/or compressive force. This is the case particularly for membranes which consist of nitrocellulose or contain nitrocellulose and/or have a pore size in the range of 0.1 to 100 micrometers diameter, particularly preferably in the range of 1 to 10 micrometers diameter.

In one preferred embodiment of the apparatus according to the embodiments, the sensor array contains or is constructed from electrochemical sensors having electrodes, in particular microelectrodes. The at least two sensors are arranged in planar fashion on a surface. Particularly preferably, the sensors are spatially separated from one another partly or completely by side walls, in particular ring-shaped side walls, in particular by side walls in the form of closed rings.

An alternative embodiment provides for the sensors to be arranged in depressions, in particular in circular depressions.

In order to achieve a high sensitivity of the measurement with the sensors, it is advantageous for the membrane to be arranged in positively locking fashion on the surface, in particular in planar fashion without bends in the membrane.

The method for the detection of liquids or substances from liquids in spatially different reaction regions or reaction spaces includes:
- filling at least one permeable or semipermeable membrane, which is arranged on a sensor array, with a liquid to be analyzed, and
- mechanically deforming the at least one permeable or semipermeable membrane in such a way that the permeability thereof is set, and
- measuring interactions of the liquid to be analyzed or substances from the liquid with sensors of the sensor array. The individual steps of the method can be carried out simultaneously or successively.

In one preferred embodiment of the method according to the embodiments, the mechanical deformation of the at least one permeable or semipermeable membrane is effected by a compressive force exerted areally on a main surface of the membrane. The compressive force can lead to compression of the membrane. This brings about, in particular, a decrease in the pore volumes. In the case of closed-off reaction spaces, the volume of the space available for the reaction decreases and, consequently, the concentration of reaction product increases with the reaction proceeding identically. The sensitivity of the measuring arrangement is thus increased.

The mechanical deformation of the at least one permeable or semipermeable membrane can result in complete prevention of liquid exchange between different regions of the membrane which are arranged adjacent to spatially separated sensors. This takes place particularly when side walls, in particular ring-shaped side walls arranged around the sensors, upon the action of pressure on the membrane in the region of the side walls, lead to a smaller pore size of the membrane, in comparison with the pore size in the region of the sensors. The formation of closed-off reaction spaces in each case for each sensor reduces or completely prevents "crosstalk", i.e. the influencing of the measurement result in one reaction space by reactions in an adjacent reaction space.

In one particularly preferred embodiment of the method of the embodiments, the filling of the at least one permeable or semipermeable membrane with liquid to be analyzed is effected by saturation of the membrane with the liquid on account of capillary forces and/or by pressure differences within the liquid.

However, the filling can also be effected by displacement of a gas from the membrane by the liquid and/or by flowing, in particularly continuous flowing, of the liquid through the membrane.

Furthermore, in one particularly preferred embodiment of the method, the measurement of interactions of the liquid to be analyzed or of substances from the liquid with sensors of the sensor array is effected by means of electrochemical measurements, in particular voltammetric and/or chronoamperometric and/or coulometric and/or impedance measurements. It is advantageous here if, during the measurement, no measurement-disturbing liquid exchange and/or substance exchange, in particular no liquid exchange and/or substance exchange at all, takes place between spatially different reaction regions which directly adjoin the sensors.

The use of the above-described apparatus and/or of the method includes the use in a smart card, in particular in a disposable smart card, including a chip, e.g. a CMOS chip having a sensor array, in particular electrochemical sensors, wherein the chip is cast in particular in a polymeric potting compound, such as e.g. plastic, and the membrane covers the chip in particular in planar fashion, particularly preferably without bends, and is in direct contract with the sensors of the chip.

In this case, the smart card can be inserted into a read-out device, in particular into a handheld read-out device, which contains, in particular, a voltage and/or current source, a display, a digital interface for the chip, a signal processing unit, an electrical, particularly preferably a thermostatically regulated electrical, tap, a plunger actuator and/or reagent actuator.

If a pressure is exerted by the read-out device on the smart card, in particular areally via a plunger, then the membrane lying on the chip is compressed in such a way that regions of the membrane that are filled with liquid to be analyzed do not exchange liquid among one another across different sensors. Therefore, closed-off reaction regions are formed in the membrane above the sensors. On account of the water-absorbent character of the membrane, however, an electrical conductivity within the membrane is at least partly still afforded.

The use of the above-described apparatus and/or of the method includes a use in an immunological fast test and/or in a blood test and/or in a DNA analysis and/or in an antibody test and/or in a peptide test.

The embodiments are based generally on the concept that a porous membrane is applied on the sensor array, via which membrane the liquid transport takes place along the surface, across the sensors. As a result of compression of the membrane, the liquid transport is prevented and closed-off reaction spaces arise above the sensors. This is primarily brought about by elevations such as walls between the sensors, which compress the membrane in the event of pressure to a greater extent in the region of the walls than in the region of the sensors. As a result, in the region of the walls, the pores of the membrane are closed and liquid transport is prevented in this region. In the region of the sensors, the pores are only reduced in size and this gives rise to closed reaction spaces having a reduced pore size and closed pores in the edge region of the reaction spaces. Liquid transport in the reaction spaces toward the sensors is possible over the pores reduced in size, while liquid transport between adjacent or spatially different reaction spaces is prevented by the closed pores. Disturbances during the measurement by liquid exchange between adjacent reaction spaces are prevented, exchange of reaction products between reaction spaces is prevented and the measurement accuracy is increased.

By virtue of the soft structure of the membrane, that is to say its compressibility, the arrangement is relatively insensitive toward fluctuations in the wall height between the sensors. In the case of walls which are somewhat higher than their neighboring walls, the membrane is compressed to a greater extent. However, the walls are not irreversibly damaged, at least as long as the pressure does not exceed a critical value and the walls are not forced through the membrane. In contrast thereto, in the case of the arrangement known in the prior art, wherein a stiff plunger is seated on the walls, no tolerance of the wall heights is possible. In the case of the arrangement known from the prior art, liquid exchange between all adjacent reaction spaces is only prevented if the incompressible plunger is conclusively in contact simultaneously with all walls. If walls are higher than others, then the plunger is in contact with them, but not with the lower walls, and liquid exchange via the lower walls is still possible. If the pressure is increased in order to achieve complete prevention of the liquid exchange between adjacent reaction spaces, the walls can be irreversibly damaged.

The abovementioned advantages associated with the apparatus according to the embodiments emerge for the method according to the embodiments and the uses according to the embodiments.

BRIEF DESCRIPTION OF THE DRAWINGS

These and other aspects and advantages will become more apparent and more readily appreciated from the following description of the exemplary embodiments, taken in conjunction with the accompanying drawings of which:

Preferred embodiments with advantageous developments in accordance with the features of the dependent claims are explained in greater detail below with reference to the following figures, but without being restricted thereto.

In the figures:

Figure 1:
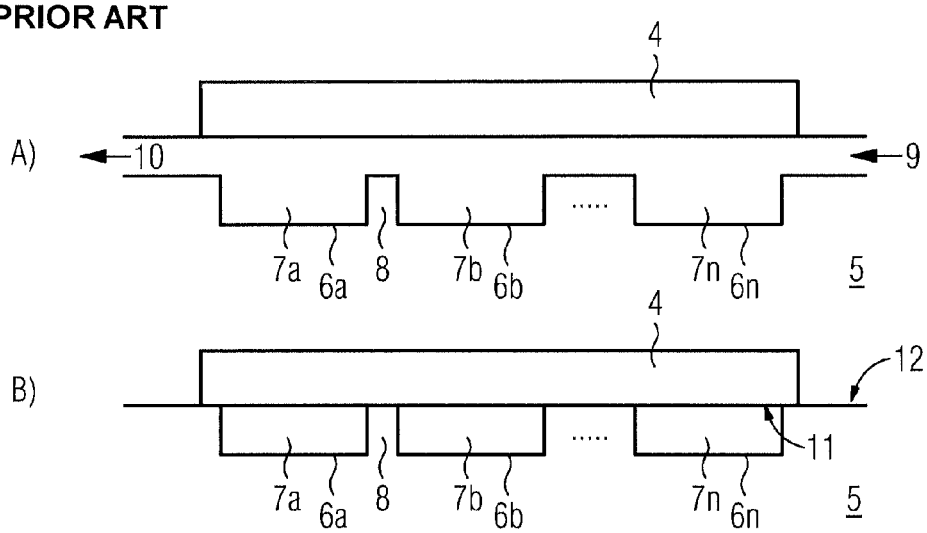
Figure 2:
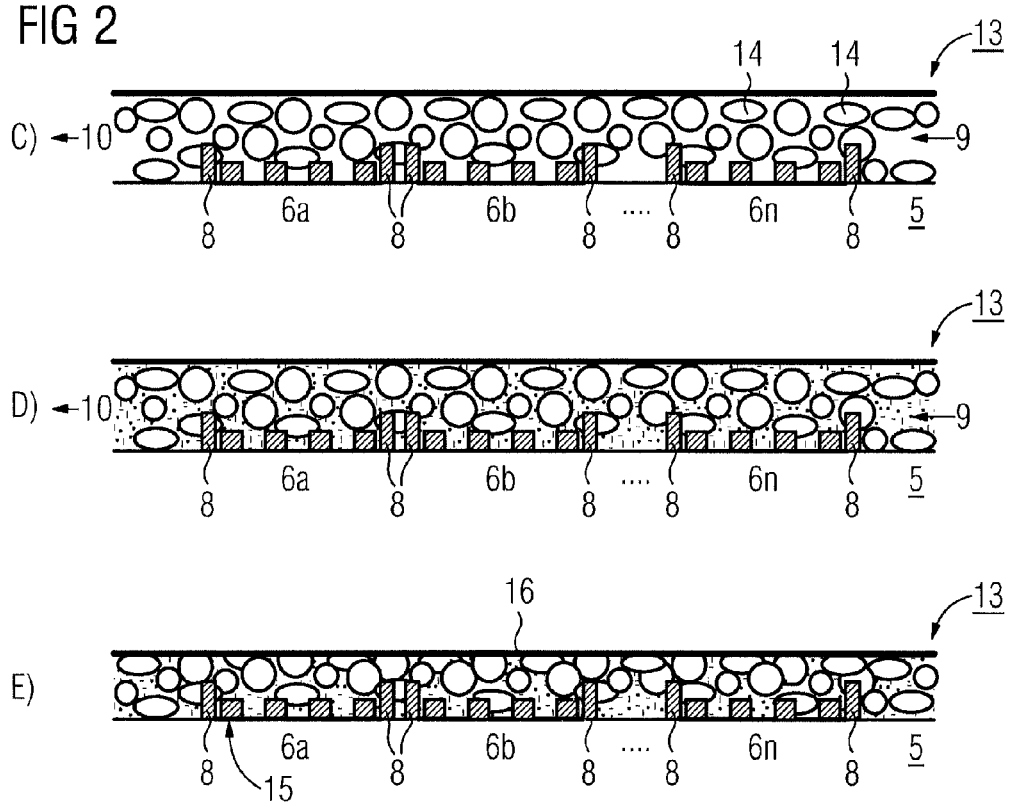
Figure 3:
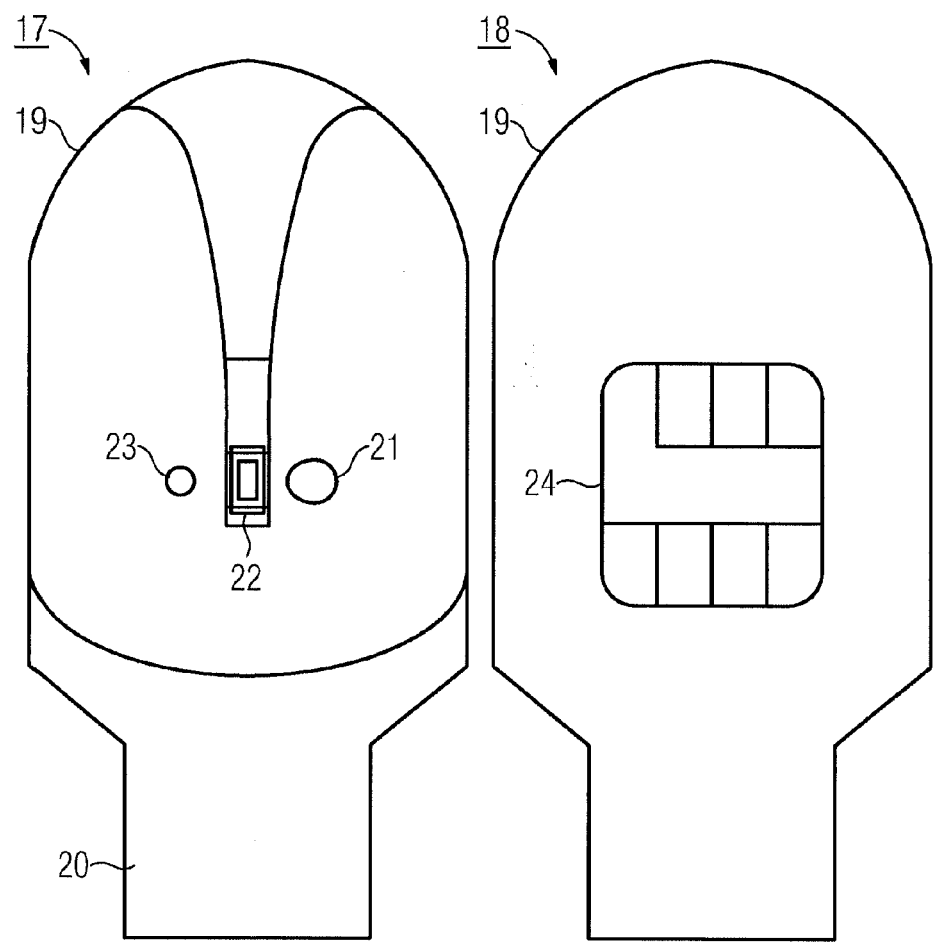
Figure 4:
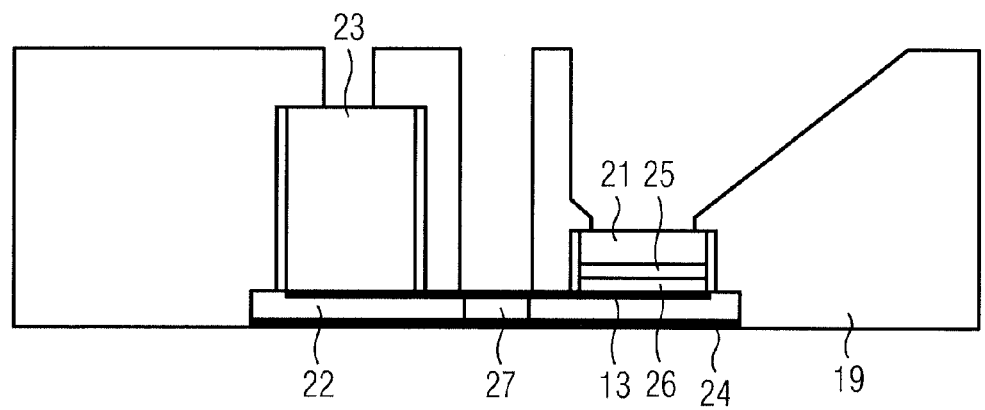
Figure 5:
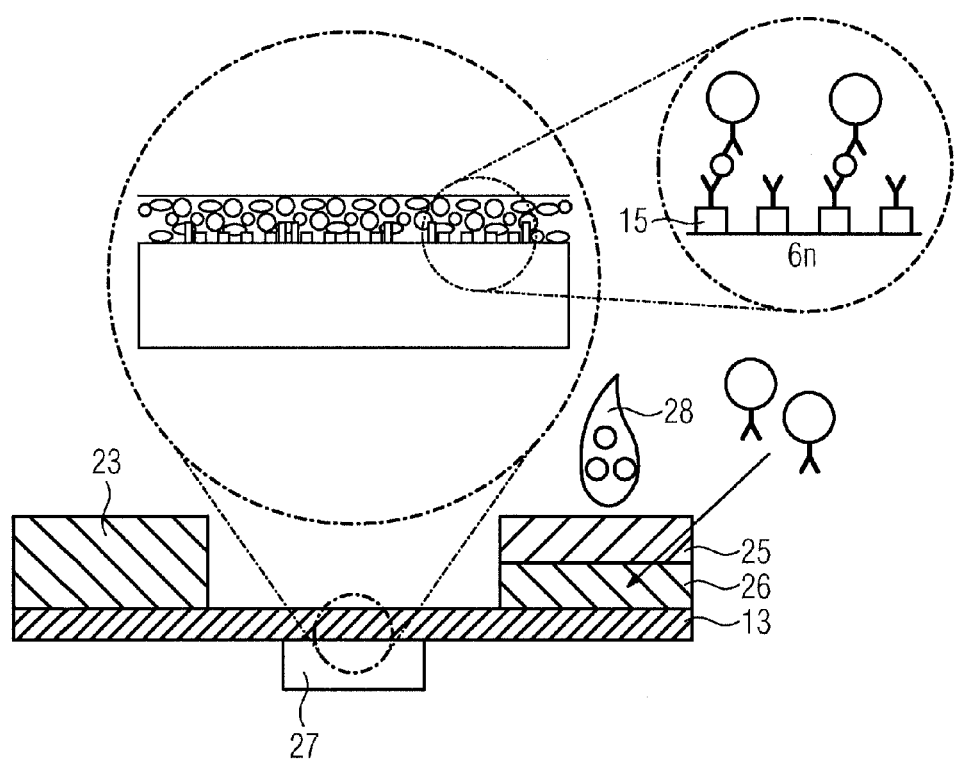

FIG. 1 shows, in two subfigures A and B, a schematic illustration of a sensor array according to the prior art with reaction spaces assigned to the sensors and with a stiff plunger for sealing the reaction spaces from liquid exchange, before and during a measurement, FIG. 2 shows, in three subfigures C to E, a schematic illustration of a sensor array of an apparatus according to the embodiments having sensors, which are spatially separated from one another by walls 8, and having a membrane lying in positively locking fashion on the surface, before and after filling with liquid and after compression during the measurement, FIG. 3 shows a schematic illustration of the front and rear sides of a plug-in module of an apparatus according to the embodiments for immunological fast tests, FIG. 4 shows a schematic illustration of a cross section through the plug-in module shown in FIG. 3, and FIG. 5 shows a simplified illustration of the cross section—shown in FIG. 4—through the plug-in module with lateral/vertical flow arrangement and CMOS chip 27.

DETAILED DESCRIPTION OF THE PREFERRED EMBODIMENT

Reference will now be made in detail to the preferred embodiments, examples of which are illustrated in the accompanying drawings, wherein like reference numerals refer to like elements throughout.

FIG. 1 illustrates an apparatus according to the prior art, such as is known e.g. from the document DE 10058394 C1, in the open state (subfigure A)) and in the closed state (subfigure B)). The apparatus includes a sensor array 5, which is constructed from sensors 6a to 6n that are spatially at a distance from one another. The sensors 6a to 6n are arranged in the form of an array on a planar surface. Between the sensors 6, walls 8 project from the planar surface. The walls 8 surround the sensors 6 completely, e.g. in the form of closed rings around each individual sensor 6a to 6n. A stiff plunger 4 is arranged at a small distance, e.g. in the range of micrometers to centimeters, parallel to the planar surface. Stiff plunger 4 in this context means a plunger composed of a material that is incompressible or compressible only to a very small extent. Liquid 28 can flow in the interspace between the stiff plunger 4 and the planar surface of the sensor array 5 with walls 8. For this purpose, microchannels can be formed in the planar surface adjacent to the sensor array 5, the microchannels serving as inlet 9 and outlet 10. If the plunger 4 is pressed in the direction of the planar surface of the sensor array 5, then it comes into direct mechanical contact with the walls 8. If the walls 8 are embodied such that they project from the planar surface with identical heights and completely enclose or encompass each sensor 6, then the plunger 4, given parallel orientation of its planar plunger surface with respect to the planar surface of the sensor array 5, is in contact with all walls 8 simultaneously and the liquid flow is completely prevented. Reaction spaces 7a to 7n are formed, which are filled with liquid 28, and which are delimited by the planar surface in which the sensors 6a to 6n are arranged, the walls 8 and the plunger 4. No liquid exchange takes place between different reaction spaces 7a to 7n. In the case of a measurement by means of the sensors 6a to 6n successively or simultaneously, different reactions in different reaction spaces 7a to 7n cannot mutually influence one another. The prevented liquid exchange between reaction spaces 7a to 7n can likewise lead to a measurement with a smaller measurement error in comparison with measurements in the case of open reaction spaces 7a to 7n.

One example of measurements by means of sensors 6 in which closed-off reaction spaces 7a to 7n lead to a reduction of measurement errors is electrochemical measurements. The sensors 6 in the case of electrochemical measurements are composed, for example, of metal electrodes 15, e.g. gold electrodes applied in a finger-shaped fashion on the planar surface. The electrodes can be coated with catcher molecules, in a manner specific to the molecules to be detected in the liquid 28. By way of example, a fixed voltage is applied to the sensors 6, that is to say gold electrodes, and a current flow to be measured changes depending on molecules binding to the surface. Further known electrochemical methods are cyclic voltammetry, chronoamperometry, coulometry, impedance spectroscopy, which differ in the measurement variables to be controlled by open-loop or closed-loop control and/or in the open-loop or closed-loop control methods for current and voltage. What is common to the methods is that the measurement results depend greatly on whether the liquid 28 to be measured is present in a stationary fashion or as a flow above the sensors 6. A simple measurement with no disturbing measurement signals is possible only in the case of a stationary liquid 28 or liquid 28 that flows in a constant fashion. The simplest measurement set-up that can be realized technically consists in the realization of a stationary liquid 28, such as is present e.g. in the apparatus shown in subfigure B of FIG. 1.

However, in order to realize a stationary liquid 28 without flows during a measurement, the reaction spaces 7a to 7n have to be completely separated from one another. This is only the case if the plunger 4 is in close contact simultaneously with all walls 8 and there is no distance between any wall and the plunger 4. This is only possible if all walls 8 project from the planar surface of the sensor array 5 with the same height. Such an apparatus presupposes very complex production methods and precise inspection of the dimensions after the production of the apparatuses.

FIG. 2 illustrates an apparatus in accordance with one exemplary embodiment of the invention in the open/dry state (subfigure C), in the open/filled state (subfigure D), and in the closed state (subfigure E). Parts that are not explained in greater detail are known per se, e.g. from the prior art mentioned. A sensor array 5, constructed from sensors 6a to 6n that are spatially separated from one another, is arranged in a planar surface on a substrate. The sensors 6 are composed e.g. of gold electrodes arranged in a finger-shaped fashion. FIG. 2 illustrates a section through the apparatus, and thus through the finger-shaped electrodes 15. Further electrode materials which can be used are metals such as e.g. silver or silver chloride paste, palladium, copper, platinum or platinized platinum, semiconductor materials such as e.g. titanium oxide or silicon, materials such as e.g. graphite, glass carbon and compounds of the materials mentioned. Walls 8 are arranged between the electrodes 15, the walls separating the electrodes 15 spatially from one another, at least in the planar plane. The walls 8 can be embodied in the form of closed rings lying flat on the planar surface, or in the form of rectangular boundaries (analogously to the boundaries of the squares on a chessboard), or in the form of triangular boundaries, or in the form of a honeycomb structure. Structures which span the area as completely as possible like a network are preferred.

The walls 8 are preferably formed from the same material as the carrier substrate on which the electrodes 15 are arranged. Possible materials are silicon, silicon oxide, plastic, glass or photoresist e.g. PBO (polybenzoxazole). However, the embodiments are not restricted to these materials. The walls 8 can also be composed of different materials than the carrier material.

They can be etched or stamped from the surface, vapor-deposited or sputtered, or applied in the form of photoresist. However, the embodiments are not restricted to walls 8 produced according to the methods mentioned above. A large number of further methods are conceivable. One further method is to arrange the sensors 6 in depressions in the surface, in an area parallel to the planar surface. The walls 8 and the carrier material are preferably not permeable to liquid.

A porous membrane 13 is arranged in positively locking fashion on the planar surface of the sensor array 5. In this context, membrane 13 should be understood to mean a thin layer which, depending on external influences such as e.g. pressure, with regard to liquid 28, it can be permeable, semipermeable (only permeable to specific portions of the liquid 28, not permeable to all substances in the liquid 28) or non-permeable (impermeable). Pores in the membrane 13 that are connected to one another provide for permeability toward liquids 28 in the relaxed state. Relaxed state should be understood to mean that no additional pressure is exerted on the membrane 13 and the membrane 13 is not depressed. Only the air pressure acts on the membrane 13. An example of a material from which the membrane 13 is constructed is nitrocellulose. Further possibilities are porous, reversibly and/or irreversibly compressible materials such as e.g. treated plastic or rubber layers or films, natural rubber, foams or fiber materials such as e.g. cotton or glass fibers.

The first subfigure of FIG. 2, subfigure C, shows the porous membrane 13 in a relaxed state. Pores are present between the membrane parts 14 from which the membrane 13 is constructed. These pores merge into one another, such that substance transport, such as e.g. a gas flow or a liquid flow, can take place via the pores. Typical orders of magnitude of the pores are in the range of nanometers to millimeters for the diameter of the pores, in particular in the range of 0.1 to 100 micrometers diameter, particularly preferably in the range of 1 to 10 micrometers diameter. In subfigure C, the pores are filled with air. The membrane 13 is fitted in positively locking fashion on the surface, that is to say that there are no cavities or no other substances are situated between the membrane 13 and the surface with walls 8 and electrodes 15. The membrane 13 has the inverse form at its side facing the planar surface with respect to the form of the surface with electrodes 15 and walls 8 arranged thereon. On that side of the membrane 13 which faces away from the planar surface, the membrane 13 shown in the exemplary embodiment illustrated is level, that is say without elevations projecting from a planar surface. However, other forms of the membrane 13 are also possible. The membrane 13 is preferably embodied like a thin film applied in positively locking fashion on the surface.

The second subfigure of FIG. 2, subfigure D, shows the membrane 13 in a relaxed state, filled with liquid 28. Liquid 28 can be fed to the membrane 13 and discharged from the membrane 13 via an inlet 9 and outlet 10, respectively. The inlet 9 and outlet 10 can be implemented parallel to the planar surface, as shown in FIG. 2, or perpendicular to the planar surface as in FIG. 5. A liquid flow in the membrane 13, with a flow direction preferably parallel to the planar surface, is possible through the entire membrane 13. The membrane 13 can be filled completely or only partly with liquid 28. In this context, partly means that e.g. air inclusions are present in the membrane 13. Filled completely means that the pores between the membrane parts 14 are filled completely with liquid 28. The filling of the membrane 13 with liquid 28 can be effected, inter alia, on account of pressure differences or on account of capillary forces.

The third subfigure of FIG. 2, subfigure E, shows the membrane 13 in a compressed state. The thickness of the membrane 13 is decreased by a pressure which is exerted areally on the membrane 13, e.g. by a plunger (not shown), perpendicular to the planar surface. Another possibility for reducing the membrane thickness is to pull the membrane 13 along a direction parallel to the planar surface. The pore size of the membrane 13 decreases in both cases. In the region perpendicular to the planar surface above the walls 8, the pore size is decreased to such a great extent that the pores completely disappear or at least the pores no longer merge into one another. Between the pores, membrane parts 14 are arranged in such a way that there is no longer a connection between adjacent pores. Gas or liquid transport in this region is completely or largely prevented. However, an electrical conductivity can still be present in this region, here in a very high-impedance form. The latter is sufficient for high-impedance potential measurements, but unsuitable for the formation of lateral electric currents (parallel to the sensor array 5 surface). In the region perpendicular to the planar surface above the sensors 6, the pores are only reduced in size, but they are still in direct contact among one another. Gas or liquid transport and electrical conductivity in this region are possible. The liquid 28 can thus be transported to and away from the sensors 6 in this region.

Reaction spaces 7 in which liquid transport is possible arise in the region perpendicular to the planar surface above the sensors 6. They are bounded by the planar surface on which the sensors 6 are arranged, by the walls 8, by the regions perpendicular to the planar surface above the walls 8 with closed pores, and by the surface of the membrane 13 on the side 16 lying opposite the planar surface. No or only very greatly restricted liquid transport takes place between adjacent reaction spaces 7. As a result, reactions can take place in the reaction spaces 7 which are not influenced or are influenced only very little by reactions in adjacent reaction spaces 7.

In the case of the compressed membrane 13 filled with liquid 28 as shown in third subfigure E of FIG. 2, measurements at the sensors 6 can take place with a smaller measurement error than in the case of the uncompressed membrane 13 filled with liquid 28 as shown in second subfigure D of FIG. 2. Flows parallel to the planar surface across a plurality of different sensors 6a to 6n are prevented or greatly restricted in the case of the compressed membrane 13. Chemical "crosstalk", that is to say the alteration of the measurement result at one sensor 6 by reactions above another sensor 6, are prevented or at least greatly restricted.

Examples of liquids 28 which can be examined by means of the apparatus illustrated are body fluids such as blood or urine or saliva, whose constituents or reaction products after e.g. disintegration reactions are detected. By way of example, DNA molecules or fragments can thus be detected or analyzed with the aid of the sensors 6, and viruses or antibodies, peptides or other biochemical compounds can be examined.

As liquids 28, however, it is also possible to examine waste water with chemical contaminants or drinking water or detect other chemical substances in liquids 28.

In FIGS. 3 to 5, a plug-in module for immunological fast tests is indicated as a possible application of the apparatus and of the method.

In this case, FIG. 3 shows the front side 17 and rear side 18 of the plug-in module, which is composed e.g. of a plastic body as housing 19 and, situated therein, a chip module 22 with a sensor array 5 on a chip 27, electrical contacts 24, and a membrane 13 situated on the chip 27. The plug-in module can have the form illustrated in FIG. 3 or other forms, such as e.g. that of a check card. Chambers and microchannels for the take-up, transport and reactions and also release of the liquid 28 are formed in the plastic housing 19. Chambers for reagents, such as dry reagents, for example, which are required for disintegration and detection reactions, for example, can likewise be realized in the plastic housing 19.

For better handling, the housing 19 can be equipped with a handle 20 and with inscriptions, such as e.g. patient or sample data. As an alternative, data can be stored on the chip 27, which is e.g. a CMOS chip (Complementary Metal Oxide Semiconductor), with a sensor array 5 situated thereon and a data processing and/or memory device integrated in the chip 27.

Liquid 28 is supplied to the housing 19 via an inlet 21 in the housing 19. The liquid 28 is conducted through the membrane 13 over the chip 27 and the sensor array 5. Before the measurement begins, a pressure is exerted on the membrane 13 by means of a plunger, which pressure is maintained during the measurement. Excess liquid 28 and also liquid 28 after the measurement, when the pressure on the membrane 13 has been canceled, can be disposed of in an outlet 23 with venting or can be removed from the housing 19 via the outlet.

The pressure on the membrane 13 during the measurement can be exerted on the membrane 13 directly via an opening in the housing 19 with the aid of a plunger, or indirectly by means of the housing 19, which then presses onto the membrane 13. The plunger is integrated in a measuring apparatus (not illustrated) comprising the measuring electronics.

The sensor array 5 is contact-connected via the chip 27 and electrical contacts 24 which are electrically connected to the chip 27 and are situated on the rear side of the housing. When the plug-in module is inserted into the measuring apparatus, electrical contact between the measuring apparatus and the electrical contacts 24 of the plug-in module is established. The sensor array 5 can be electrically addressed via the measuring electronics of the measuring apparatus, and measurement variables can be communicated to the measuring electronics, which are then processed and evaluated in the measuring apparatus. A display or other optical and acoustic output devices, which are connected to the measuring apparatus, can output the measurement result.

FIG. 4 illustrates a section through the plug-in module shown in FIG. 3. An enzyme substrate pad 25, a conjugate pad 26, the chip module 22 with a sensor array 5 on e.g. a CMOS chip 27 and also the membrane 13 arranged thereon are integrated in the housing 19. The liquid 28 to be examined, e.g. blood 28, can be supplied via a liquid inlet 21. As illustrated in more detail in FIG. 5, the liquid 28 flows through an enzyme substrate pad 25 and a conjugate pad 26, for example. Further substance pads can also be integrated, which mix the liquid 28 to be examined with chemical substances and prepare it for the examination by means of chemical reactions.

In the example illustrated in FIG. 5, the blood is disintegrated, that is to say that the cells release constituents such as DNA, for example, which are in turn decomposed into small fragments. The fragments are subsequently bound to markers that enable the fragments to be detected.

The liquid 28 prepared in this way is conducted through the membrane 13, that is to say that, by means of capillary forces and/or an external pressure or gravitational forces, the liquid 28 is sucked up by the membrane 13 and/or the membrane 13 is filled with the liquid 28. The membrane 13 is in direct contact with the sensor array 5 or is arranged on the latter. The liquid 28 is thus conducted over the sensor array 5. An opening in the housing 19 above the chip 27 with the membrane 13 arranged thereon enables a pressure to be applied to the membrane 13, e.g. by means of a plunger, which presses onto the membrane 13. The pressure is dimensioned such that, in regions with walls 8 on the sensor array 5, the pores of the porous membrane 13 close completely, without the walls 8 being damaged by an excessively high pressure. In regions directly above the sensors 6, the pores are reduced in size in comparison with their original size before pressure is applied to the membrane 13. However, they are not completely closed in the region directly above the sensors 6, in contrast to the case in the region above the walls 8. Closed-off reaction spaces 7 separated from one another, in which reactions can proceed, arise in the membrane 13 filled with liquid 28. Sensors 6 in the reaction spaces 7 can register and detect reaction products in a manner uninfluenced by reactions in adjacent reaction spaces 7. Liquid flows across a plurality of reaction spaces 7 are prevented and do not lead to interference signals during the measurement or to measurement errors.

After the reactions and the measurements with the aid of the sensors 6 have proceeded, the pressure on the membrane 13 is canceled, and the liquid 28 can flow into a liquid outlet 23. It can remain there or be removed for further examinations. The liquid outlet 23 likewise serves for disposing of an excess amount of liquid before the measurements and for disposing of e.g. purging liquids that are used before and after measurements for purging the membrane 13.

The plug-in module can be designed for single use, that is to say as a disposable module, or for repeated use.

The system also includes permanent or removable storage, such as magnetic and optical discs, RAM, ROM, etc. on which the process and data structures can be stored and distributed. The processes can also be distributed via, for example, downloading over a network such as the Internet. The system can output the results to a display device, printer, readily accessible memory or another computer on a network.

A description has been provided with particular reference to preferred embodiments thereof and examples, but it will be understood that variations and modifications can be effected within the spirit and scope of the claims which may include the phrase "at least one of A, B and C" as an alternative expression that means one or more of A, B and C may be used, contrary to the holding in *Superguide* v. *DIRECTV,* 358 F3d 870, 69 USPQ2d 1865 (Fed. Cir. 2004).

The invention claimed is:

1. A method for detection of liquids or substances from liquids with sensors in spatially different reaction regions, the sensors being spatially separated from one another at least partially by side walls, comprising the steps of:
    producing a flow of the liquid filling at least one permeable or semipermeable membrane including pores of the membrane, which is arranged over a sensor array, with a sample of a liquid to be analyzed;
    mechanically deforming the at least one permeable or semipermeable membrane in such a way that the permeability thereof is reduced so as to compress the membrane forcing portions of the liquid from the membrane into said spatially different reaction regions; and
    measuring interactions of the sample of the liquid to be analyzed or of substances from the sample of the liquid with sensors of the sensor array as the different portions of the sample of the liquid flow in parallel into the spatially different reaction regions to the sensors of the sensor array in the different spatially different reaction regions.

2. The method as claimed in claim 1, wherein at least two of the filling, mechanically deforming and measuring are carried out simultaneously or successively.

3. The method as claimed claim 1, wherein the mechanical deformation of the at least one permeable or semipermeable membrane is effected by a compressive force exerted on a main surface of the membrane by a plunger.

4. The method as claimed in claim 1, wherein complete prevention of liquid exchange between different regions of the membrane is effected by side walls which are ring-shaped side walls arranged around the sensors, wherein the side walls, upon action of pressure on the membrane in the region of the side walls, lead to a smaller pore size of the membrane, in comparison with the pore size in a region of the sensors.

5. The method as claimed in claim 4, wherein the filling of the at least one permeable or semipermeable membrane with the sample of the liquid to be analyzed is effected by saturation of the membrane with the liquid on account of capillary forces and/or by pressure differences within the liquid.

6. The method as claimed in claim 1,
    wherein the filling of the at least one permeable or semipermeable membrane with the sample of the liquid to be analyzed is effected by displacement of a gas from the membrane by the sample of the liquid and/or by continuous flowing of the sample of the liquid through pores of the membrane on account of a pressure difference or on account of capillary forces.

7. The method as claimed in claim 6, wherein the measurement of interactions of the sample of the liquid to be analyzed or of substances from the sample of the liquid with sensors of the sensor array is effected by electrochemical measurements comprising voltammetric and/or amperometric and/or coulometric and/or impedance measurements and/or by redox cycling.

8. The method as claimed in claim 7, wherein, during the measurement of interactions of the sample of the liquid to be analyzed or of substances from the sample of the liquid with sensors of the sensor array, no measurement-disturbing liquid exchange and/or substance exchange takes place between spatially different reaction regions which directly adjoin the sensors.

9. The method as claimed in claim 1, wherein the method is used in a disposable smart card or disposable cassette, comprising a CMOS chip comprising a sensor array comprising electrochemical sensors, wherein the chip is cast in a polymeric potting compound comprising plastic, and the membrane covers the chip in planar fashion without bends, and is in direct contract with the sensors of the chip.

10. The method as claimed in claim 9, wherein the smart card or cassette is inserted into a read-out device, comprising a handheld read-out device, which contains a voltage and/or current source, a display, a digital interface for the chip, a signal processing unit, an electrical thermostatically regulated electrical tap, a plunger actuator and/or reagent actuator.

11. The method as claimed in claim 10, wherein a pressure is exerted by the read-out device on the smart card or cassette via a plunger, and the membrane lying on the chip is compressed in such a way that regions of the membrane that are filled with the sample of the liquid to be analyzed do not exchange liquid among one another across different sensors, where closed-off reaction regions are formed in the membrane above the sensors and/or pore volumes are decreased.

12. The method as claimed in claim 11, wherein the method is used in an immunological fast test and/or in a blood test and/or in a DNA analysis and/or in an antibody test and/or in a peptide test.

* * * * *